(12) United States Patent
Masterson et al.

(10) Patent No.: US 10,371,378 B2
(45) Date of Patent: Aug. 6, 2019

(54) METHOD AND APPARATUS FOR MONITORING PORT BLOCKAGE FOR TDLAS MEASUREMENTS IN HARSH ENVIRONMENTS

(71) Applicant: John Zink Company, LLC, Tulsa, OK (US)

(72) Inventors: Bernard P Masterson, Louisville, CO (US); Michael John Estes, Longmont, CO (US); Andrew D Sappey, Lakewood, CO (US)

(73) Assignee: John Zink Company, LLC, Tulsa, OK (US)

( * ) Notice: Subject to any disclaimer, the term of this patent is extended or adjusted under 35 U.S.C. 154(b) by 350 days.

(21) Appl. No.: 15/104,795

(22) PCT Filed: Dec. 22, 2014

(86) PCT No.: PCT/US2014/071839
§ 371 (c)(1),
(2) Date: Jun. 15, 2016

(87) PCT Pub. No.: WO2015/095861
PCT Pub. Date: Jun. 25, 2015

(65) Prior Publication Data
US 2016/0313003 A1    Oct. 27, 2016

Related U.S. Application Data

(60) Provisional application No. 61/919,228, filed on Dec. 20, 2013.

(51) Int. Cl.
*F23N 5/08* (2006.01)
*F23N 5/24* (2006.01)
(Continued)

(52) U.S. Cl.
CPC ........... *F23N 5/082* (2013.01); *F23M 11/042* (2013.01); *F23N 5/24* (2013.01); *G01N 21/15* (2013.01);
(Continued)

(58) Field of Classification Search
CPC ......... F23M 11/042; F23N 5/082; F23N 5/08; F23N 5/24; G01N 21/15; G01N 21/39;
(Continued)

(56) References Cited

U.S. PATENT DOCUMENTS 4,794,266 A    12/1988  Saari
4,896,047 A     1/1990  Weaver et al.
(Continued)

FOREIGN PATENT DOCUMENTS

CN        1171082 C     10/2004
CN      101287976 B      9/2010
(Continued)

OTHER PUBLICATIONS

Office Action dated Feb. 22, 2018, for corresponding Chinese application No. CN105917170A, 16 pages (including translation).
(Continued)

*Primary Examiner* — Sang H Nguyen (57) ABSTRACT

A method of monitoring blockage of a sight tube attached to a wall of a process chamber, the sight tube being operatively associated with a TDLAS optical head with a window between the sight tube and the TDLAS optical head. The method includes the steps of providing a photo sensor in the TDLAS optical head, the photo sensor being positioned to receive light emitted by a light emitting process within the process chamber. An emission signal produced by light emitted by the light emitting process within the process chamber being received by the photo sensor is monitored. A determination is made if the emission signal is degrading.

14 Claims, 4 Drawing Sheets

(51) Int. Cl.
*F23M 11/04* (2006.01)
*G01N 21/15* (2006.01)
*G01N 21/39* (2006.01)
*G01N 21/71* (2006.01)
*G01N 21/84* (2006.01)

(52) U.S. Cl.
CPC .......... *G01N 21/39* (2013.01); *G01N 21/716* (2013.01); *F23N 2031/00* (2013.01); *G01N 2021/151* (2013.01); *G01N 2021/152* (2013.01); *G01N 2021/399* (2013.01); *G01N 2021/8416* (2013.01); *G01N 2201/066* (2013.01); *G01N 2201/0826* (2013.01); *G01N 2201/0833* (2013.01)

(58) Field of Classification Search
CPC .......... G01N 21/716; G01N 2021/151; G01N 2021/152; G01N 2021/399; G01N 2021/8416; G01N 2021/066; G01N 2021/0833; G01N 2021/0826
See application file for complete search history.

(56) References Cited

U.S. PATENT DOCUMENTS

| | | | |
|---|---|---|---|
| 5,046,138 A | 9/1991 | Grubb, III | |
| 5,070,823 A | 12/1991 | Ackerman | |
| 7,248,755 B2 | 7/2007 | Sappey et al. | |
| 8,544,334 B2* | 10/2013 | Jo | G01L 19/0007 73/700 |
| 8,786,857 B2* | 7/2014 | Masterson | F02C 7/00 356/437 |
| 2003/0218585 A1 | 11/2003 | Hoshi | |
| 2005/0173375 A1 | 8/2005 | Mitrovic | |
| 2005/0263047 A1 | 12/2005 | Bergmyren | |
| 2006/0192968 A1 | 8/2006 | Farrant | |
| 2008/0074645 A1* | 3/2008 | Sappey | G01J 3/02 356/51 |
| 2008/0204720 A1* | 8/2008 | Howell | G01J 3/02 356/73 |
| 2008/0289342 A1* | 11/2008 | Sappey | F01D 21/003 60/793 |
| 2009/0015824 A1 | 1/2009 | Shubinsky | |
| 2011/0083447 A1 | 4/2011 | Zurecki | |
| 2011/0300492 A1* | 12/2011 | Estes | F23M 5/08 431/2 |
| 2013/0195245 A1* | 8/2013 | Sivathanu | G01N 23/04 378/54 |
| 2014/0238032 A1* | 8/2014 | Fitzgerald | F02C 9/26 60/772 |

FOREIGN PATENT DOCUMENTS

| | | |
|---|---|---|
| WO | 2004/068069 A1 | 8/2004 |
| WO | WO 2013/158311 | 10/2013 |

OTHER PUBLICATIONS

Supplemental European Search Report for Application No. EP 14872360.4 dated Jul. 26, 2017.
Examination Report dated Oct. 15, 2018, for corresponding EP application No. 14872360.4, 5 pages.
Office Action dated Nov. 6, 2018, for corresponding CN Application No. 2014800734747, 20 pages—including translation.
Office Action dated Oct. 19, 2018, for corresponding JP Application No. 2016-541179, 20 pages—including translation.

* cited by examiner

METHOD AND APPARATUS FOR MONITORING PORT BLOCKAGE FOR TDLAS MEASUREMENTS IN HARSH ENVIRONMENTS

RELATED APPLICATIONS

This application is a 35 U.S.C. § 371 national phase application of PCT/US14/71839 (WO 2015/095861), filed on Dec. 22, 2014, entitled "Method and Apparatus for Monitoring Port Blockage for TDLAS Measurements in Harsh Environments", which application claims the benefit of U.S. Provisional Application Ser. No. 61/919,228, filed Dec. 20, 2013, each of which is incorporated herein by reference in its entirety.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

TECHNICAL FIELD

The present invention is directed toward a method and apparatus for monitoring port blockage in harsh environments and more particularly toward a method and apparatus for monitoring port blockage for tunable diode laser absorption spectroscopy measurements used to monitor and control combustion processes.

BACKGROUND

Tunable diode laser absorption spectroscopy ("TDLAS") has been used to monitor and control processes in a wide variety of combustion and process chambers. TDLAS measurements require a clear line of sight for transmission of a laser beam through the environment being sensed. In many industrial applications, keeping a clear line of sight can be an issue. For instance, in coal-fired power plants, slag and ash can build up in or on sight tube openings to the furnace that provide the necessary line of sight, effectively blocking the laser beam. In steel reheat furnaces or electric arc furnaces, friable refractory and scale can build up in or on sight tubes providing the line of sight access and in electric arc furnaces, molten metal, slag or dust can block the sight tubes. Steam methane reformers, basic oxygen furnaces for steel making, glass furnaces, ethylene cracking furnaces, refinery process furnaces or any other type of industrial furnace, particularly those having a friable refractory, can have similar port blockage issues. All such furnaces and process chambers referred to in this paragraph constitute "process chambers" as used herein.

In addition to port blockage issues, there are other problems that can cause a loss of laser beam transmission in these environments. For instance, in all of the applications listed above, the process chambers or duct walls are mechanically dynamic. Thus, alignment between the laser transmission and receive optics can be difficult to maintain. This can be overcome by the use of automatic alignment systems, for example as described in U.S. Pat. No. 7,248,755. In addition, the particle loading in certain environments, in particular in electric arc furnaces, basic oxygen furnaces and coal-fired furnaces, can be sufficiently high under certain circumstances that no light can be detected (sometimes referred to herein as "high opacity") leading to a loss of light transmission and the corresponding measurements of such light. In addition, the optical windows separating the TDLAS optics from the process chamber can become fouled, leading to a loss of light transmission. Because the precise cause of a loss of laser beam transmission can be difficult to determine, misdiagnosis of system issues is common and can lead to unnecessary service and maintenance costs. The present disclosure is directed toward overcoming one or more of the problems discussed above.

SUMMARY OF THE EMBODIMENTS

A first aspect is a method of monitoring blockage of a sight tube attached to a wall of a process chamber, the sight tube being operatively associated with a TDLAS optical head with a window between the sight tube and the TDLAS optical head. The method includes the steps of providing a photo sensor in the TDLAS optical head, the photo sensor being positioned to receive light emitted by light producing process in the process chamber such as combustion. An emission signal produced by light emitted by the light producing process within the process chamber being received by the photo sensor is monitored. A determination is made if the emission signal is degrading.

Embodiments of the method can further include initiating clearing of the sight tube based on a determination that the emission signal is degrading. Embodiments may also include after clearing of the sight tube, determining if the emission signal has strengthened. Embodiments may further include initiating window cleaning based on a determination that the emission signal has not strengthened. Embodiments may further include determining if the TDLAS laser signal is degrading, based on a determination that the emission signal is not degrading. If the TDLAS laser signal is determined to be degrading, the optics of the TDLAS optical head are aligned. Embodiments may further include determining after aligning the optics of the TDLAS optical head if the TDLAS laser signal is degrading, and based on such determination producing a high opacity signal.

The step of initiating clearing of the sight tube may comprise initiating a port rodder to clear physical blockage. Thereafter, determination is made if the signal has strengthened. Embodiments may further include initiating blow down to clear physical blockage if the emission signal has not strengthened.

A second aspect of the invention is a method of monitoring blockage in a plurality of sight tubes attached to at least one wall of a process chamber, each sight tube being operatively associated with a TDLAS optical head with a window between the sight tube and the TDLAS optical head. The method includes providing a photo sensor in each TDLAS optical head, each photo sensor being positioned to receive light emitted by a light producing process (e.g., combustion) within the process chamber. An emission signal produced by light emitted by the light emitting process within the process chamber being received by each photo sensor is monitored. A determination is made if an emission signal received by one of the photo sensors is degrading. Based on a determination that the emission signal received by the one photo sensor is degrading, a determination is made if the emission signal received by the other photo sensors is degrading.

Embodiments may include, based on a determination that the emission signals received by the other photo sensors are degrading, adding a count to a counter and repeating the steps of determining if an emission signal received by one of the photo sensors is degrading, wherein, based on a determination that the emission signal received by the one photo sensor is degrading, further determining if the emission signals received by the other photo sensors are degrading. Embodiments may further include initiating clearing of the sight tube associated with the one photo sensor based on a determination that the emission signals received by the other photo sensors are not degrading.

Another aspect of the invention is a TDLAS optical head. The TDLAS optical head comprises a housing configured for attachment to a sight tube attached to a wall of a process chamber. Optics are provided within the housing for transmitting, receiving, or transmitting and receiving a TDLAS beam within a process chamber through a sight tube to which the housing is attached. A photo sensor is positioned in the housing to receive light emitted by the light producing process within a process chamber to which the housing is attached.

Various modifications and additions can be made to the embodiments discussed without departing from the scope of the invention. For example, while the embodiments described above refer to particular features, the scope of this invention also included embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Figure 1:
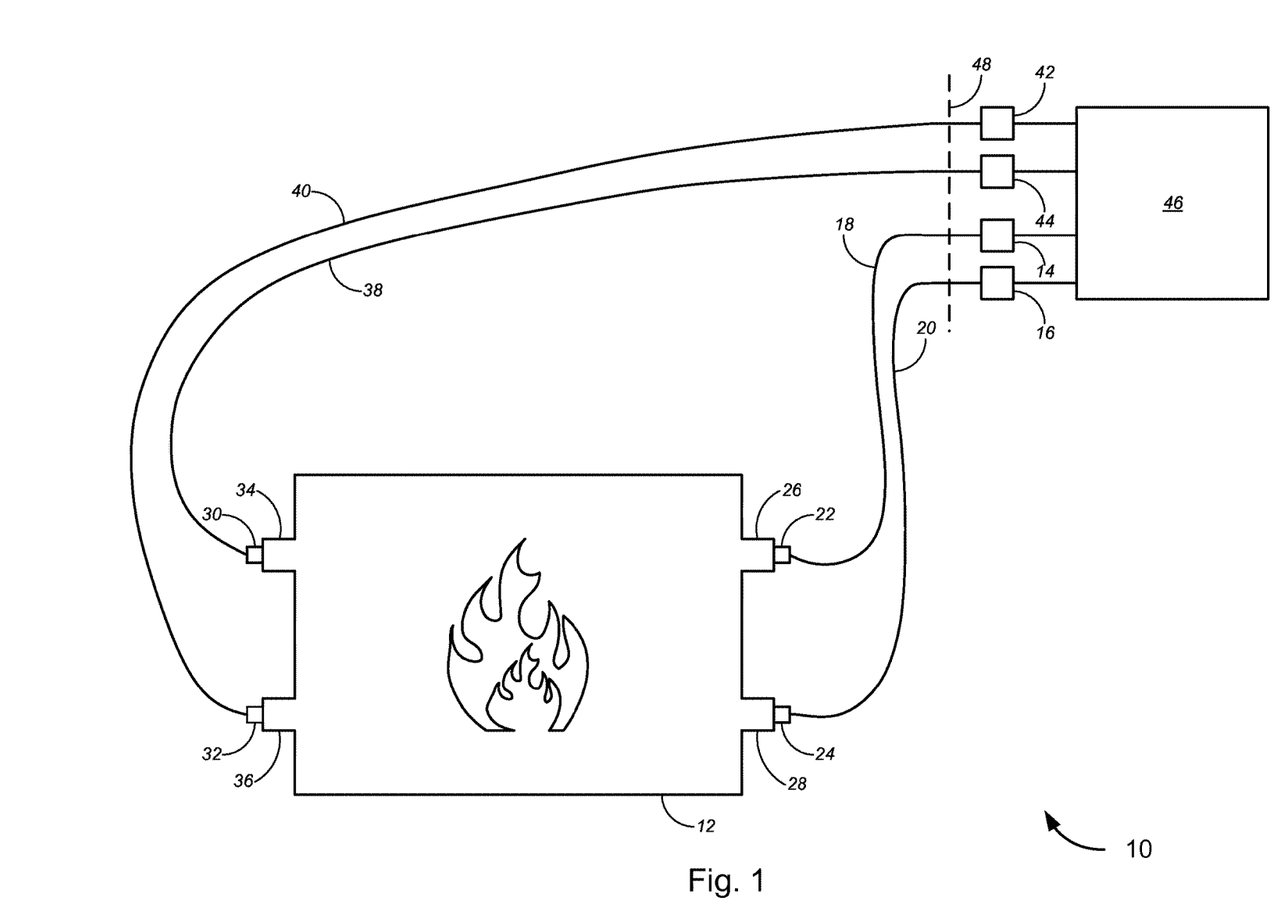
FIG. 1 is schematic representation of a process chamber, in particular a combustion chamber, having two pairs of TDLAS pitch and catch optics attached to sight tubes attached to opposing walls of the combustion chamber.

FIG. 1 schematically illustrates a sensing apparatus 10 suitable for sensing, monitoring and control of a process in a process chamber, in particular a combustion process in a combustion chamber 12. The sensing apparatus 10 performs tunable diode laser absorption spectroscopy ("TDLAS") using laser light from tunable diode lasers 14, 16 at select frequencies in the near-infrared or mid-infrared spectrum. The output of each tunable diode laser 14, 16 is coupled to an optical fiber 18, 20 which may be a single mode optical fiber or a multimode optical fiber. Multiple tunable diode lasers operating at select frequencies could also be provided with their combined beams combined by, for example, a multiplexer, as described in U.S. Pat. No. 7,248,755. As used herein, "coupled", "optically coupled" or "in optical communication with" is defined as a functional relationship between counterparts where light can pass from a first component to a second component either through or not through intermediate components or free space. The optical fibers 18, 20 are optically coupled to TDLAS optical heads 22, 24 which in turn are attached to sight tubes 26, 28 which provide optical access of the TDLAS optical heads 22, 24 to the interior of the combustion chamber 12. The TDLAS optical heads 22, 24 each contain pitch optics allowing for transmission of the laser beam through the sight tubes 26, 28 and into the combustion chamber 12 where they are optically coupled to the TDLAS optical heads 30, 32, respectively. As with the TDLAS optical heads 22, 24, the TDLAS optical heads 30, 32 are attached to sight tubes 34, 36 which in turn are attached to an opposing wall of the combustion chamber 12. The TDLAS optical heads 30, 32 have receive optics which optically couple the laser beam to the optical fibers 38, 40 which in turn are optically coupled to detectors 42, 44, which typically are photo detectors sensitive to the frequency(s) of laser light generated to form the probe beam transmitted between the pitch optics and the TDLAS optical heads 22, 24 and the catch optics of the TDLAS optical heads 30, 32. In the case a multiplexed beam is being transmitted from the pitch optics, demultiplexers can be provided for providing beams of a select wavelength to an array of detectors 42, 44. The detectors 42, 44 generate an electrical signal based on the nature and quality of the light transmitted to the detectors 42, 44 at the detector frequency.

The electrical signal from each detector 42, 44 is typically digitized and analyzed in the computer processor 46. As is known in the art, the digitized and analyzed data can be used to sense physical parameters within the combustion chamber including but not limited to the concentration of various gas species and the combustion temperature within the combustion chamber 22. The use of fiber optic coupling of the electronic and optical components on both the pitch and catch sides of the sensing apparatus 10 allows delicate temperature sensing apparatus such as the tunable diode lasers 14, 16, the detectors 42, 44 and the processor 46 to be located in a control room having an stable environment indicated by the dashed line 48. Thus, only the relatively robust pitch and catch TDLAS optical heads 22, 24, 30,32 need be situated near the hostile environment of the combustion chamber 12.

Figure 2:
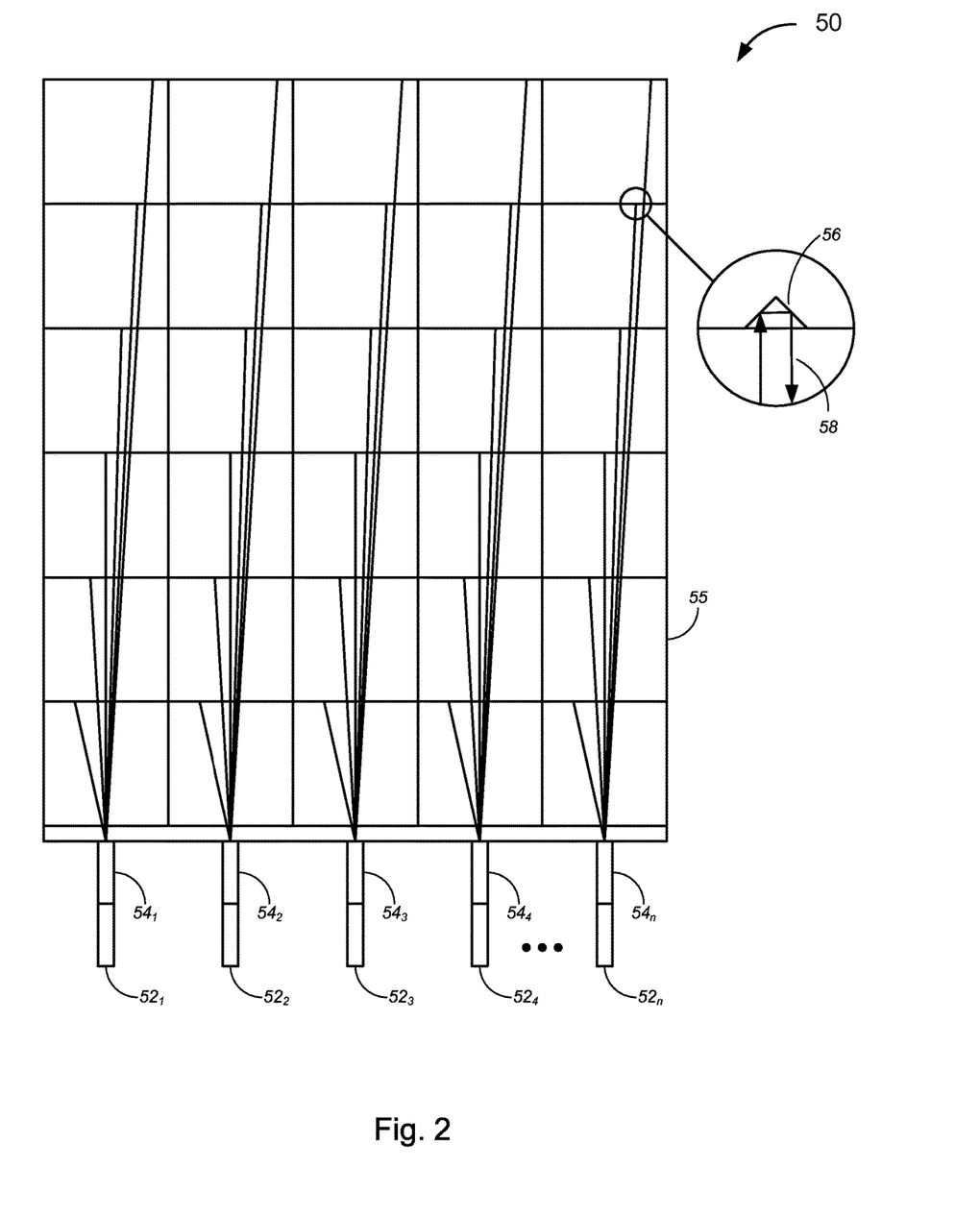
FIG. 2 is a schematic representation of an embodiment of a steerable TDLAS system with a combination pitch/catch optic used in conjunction with an array of in-furnace retroreflectors wherein combustion monitoring and control are performed in predetermined zones within the furnace.

FIG. 2 represents an alternative embodiment of a sensing apparatus 50 using a number of TDLAS optical heads $52_1$-$52_n$ wherein each of the TDLAS optical heads $52_1$-$52_n$ is coupled to a sight tube $54_1$-$54_n$ which in turn is coupled to a wall of a process chamber such a combustion chamber 55. In this embodiment, each of the TDLAS optical heads $52_1$-$52_n$ includes pitch/catch optics for both pitching and catching a laser beam. Each of the TDLAS optical heads $52_1$-$52_n$ further include an apparatus for directing the laser beams to one of a plurality of retro reflectors 56, which catch and reflect the laser beams 58 back to the TDLAS optical heads $52_1$-$52_n$. The embodiment of FIG. 2 would further include lasers, detectors and the computer processor as depicted in FIG. 1, but which have been omitted for the sake of simplicity. Such an embodiment is described in greater detail in WO 2013/158311 (PCT/US2013/032479).

Figure 3:
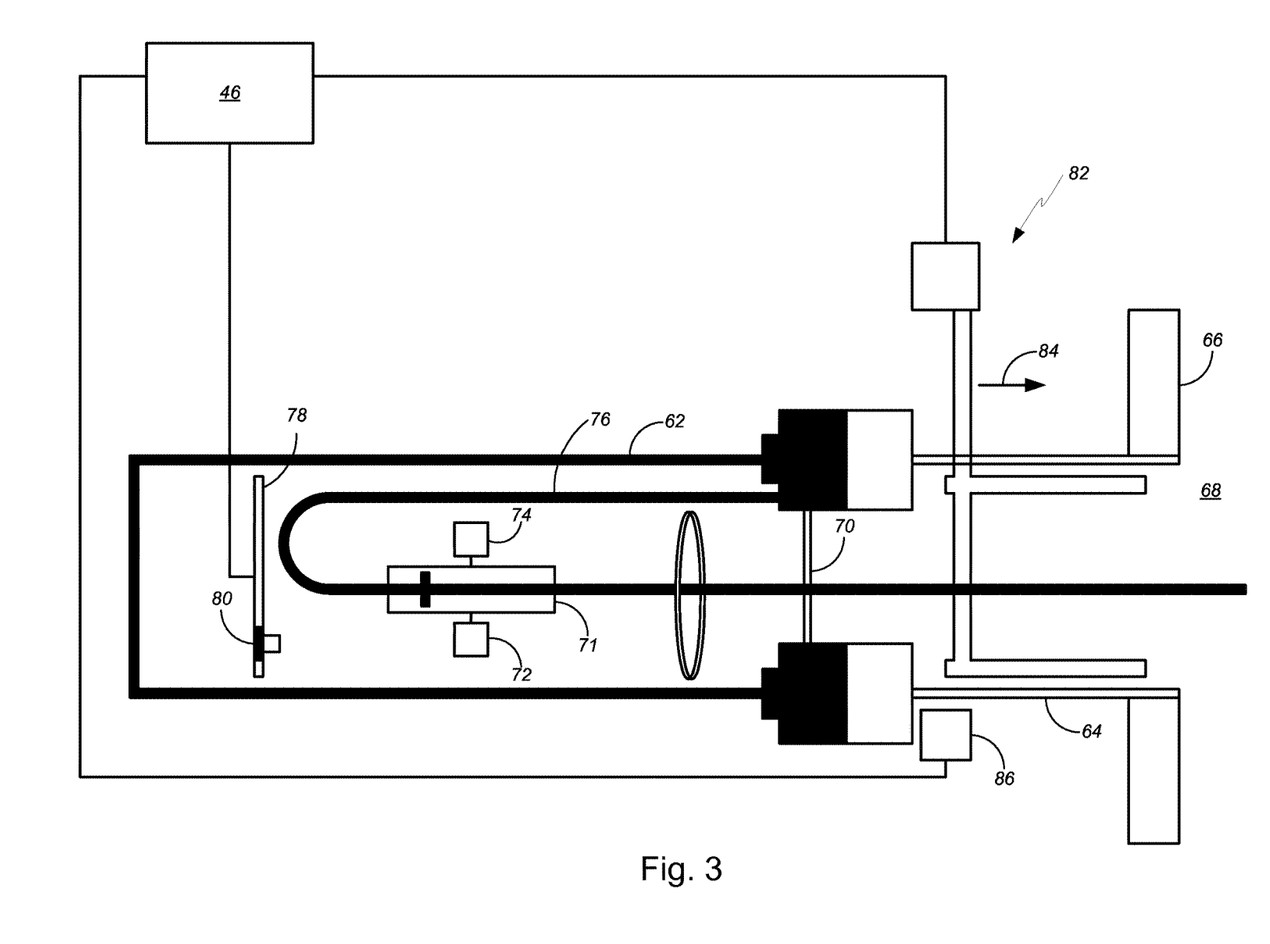
FIG. 3 is a schematic representation of a TDLAS optical head attached to a sight tube attached to a combustion chamber wall, the TDLAS optical head including an apparatus for monitoring sight tube blockage.

FIG. 3 schematically illustrates an apparatus for monitoring port blockage for use with TDLAS optical heads such as the pitch TDLAS optical heads 22, 24 and the catch TDLAS optical heads 30, 32 illustrated in FIG. 1 and the pitch/catch TDLAS optical heads $52_1$-$52_n$ depicted in FIG. 2. The apparatus for monitoring port blockage illustrated in FIG. 3 is shown in conjunction with a TDLAS optical head which comprises a TDLAS optical head housing 62 configured for attachment to a sight tube 64 attached to a wall 66 of a process chamber such as a combustion chamber 68. A window 70 separates the interior of the TDLAS optical head from the sight tube 64. Inside the TDLAS optical head housing 62 resides a fiber collimator 71 operatively associated with stepper motors 72, 74 for controlling tip-tilt of the fiber collimator 71. Optical fiber 76 is optically coupled to the fiber collimator 71 for conveying optical signals to detectors such as the detectors 42, 44, depicted in FIG. 1. The TDLAS optical head depicted in FIG. 3 is a catch TDLAS optical head, but could be a pitch TDLAS optical head or a pitch/catch TDLAS optical head depending upon the optical components included therein. Provided near a closed or proximal end of the TDLAS optical head is a head control board 78 having a photo sensor 80 coupled thereto. Operatively associated with the sight tube 64 is a port rodder 82 configured to physically remove slag or other material that might collect in the sight tube 64 by movement of the port rodder 82 in the direction of the arrow 84 to drive the debris out of the mouth of the sight tube 64 into the combustion chamber 68. Also associated with the sight tube 64 is a blow down apparatus 86 configured to, upon demand, produce a sudden burst of air to clear blockages of the sight tube 64 such as ash, dust or small pebbles. The head control board 78 and the photo sensor 80 are coupled to processor 46 for transfer of data and commands therebetween. The processor 46 is further coupled to the port rodder 82 and the blow down apparatus 86 to control their actuation. Though not shown, the processor 46 is coupled to the stepper motors 72, 74 to control alignment of the fiber collimator.

In general terms, the apparatus for monitoring port blockage works by the photo sensor 80 detecting light emitted by combustion within the combustion chamber 68. A physical blockage in a sight tube (or a dirty window) causes a partial loss or total loss of emitted light reaching the photo sensor 80 and thus of an emission signal generated by the photo sensor 80 and delivered to the processor 46. Under certain circumstances to be described below, loss of the emission signal may trigger the processor 46 to actuate the port rodder 82 in an attempt to clear debris from the sight tube 64. Alternatively or in addition, the blow down apparatus 86 may be actuated in an effort to clear debris from the sight tube 64.

The apparatus for monitoring port blockage receives light at the photo sensor 80 from a combustion process in the combustion chamber 68 that makes its way down the sight tube 64 which is not reflected or blocked by the transmit and receive optics, mount and the like within the housing 62, many of which have been removed from the schematic illustration of FIG. 3 for the sake of clarity. Under normal operating conditions, the emitted process light will fluctuate around an average value. Physical blockage in the sight tube (or a dirty window) causes a partial or total loss of this light emission signal. If the emission signal persists, but laser transmission signal is diminished, this indicates that misalignment of the optics and/or opacity within the combustion chamber 68 is the likely cause. If the emission signal decreases from its average value, it may be due to a physical blockage in the port or a dirty window. The temporal history of the emissions signal can provide clues as to whether a dirty window or physical blockage is the issue, since dirty windows typically degrade over time with both the laser transmission signal and the emission signal affected equally with the same temporal history. Physical blockage tends to occur relatively instantaneously relative to the time scale of window fouling. In the event the signals from the photo sensor 80 of one or more TDLAS optical heads indicates a port blockage, the port rodder 82 and/or the blow down apparatus 86 can be actuated to try to alleviate the blockage.

Figure 4:
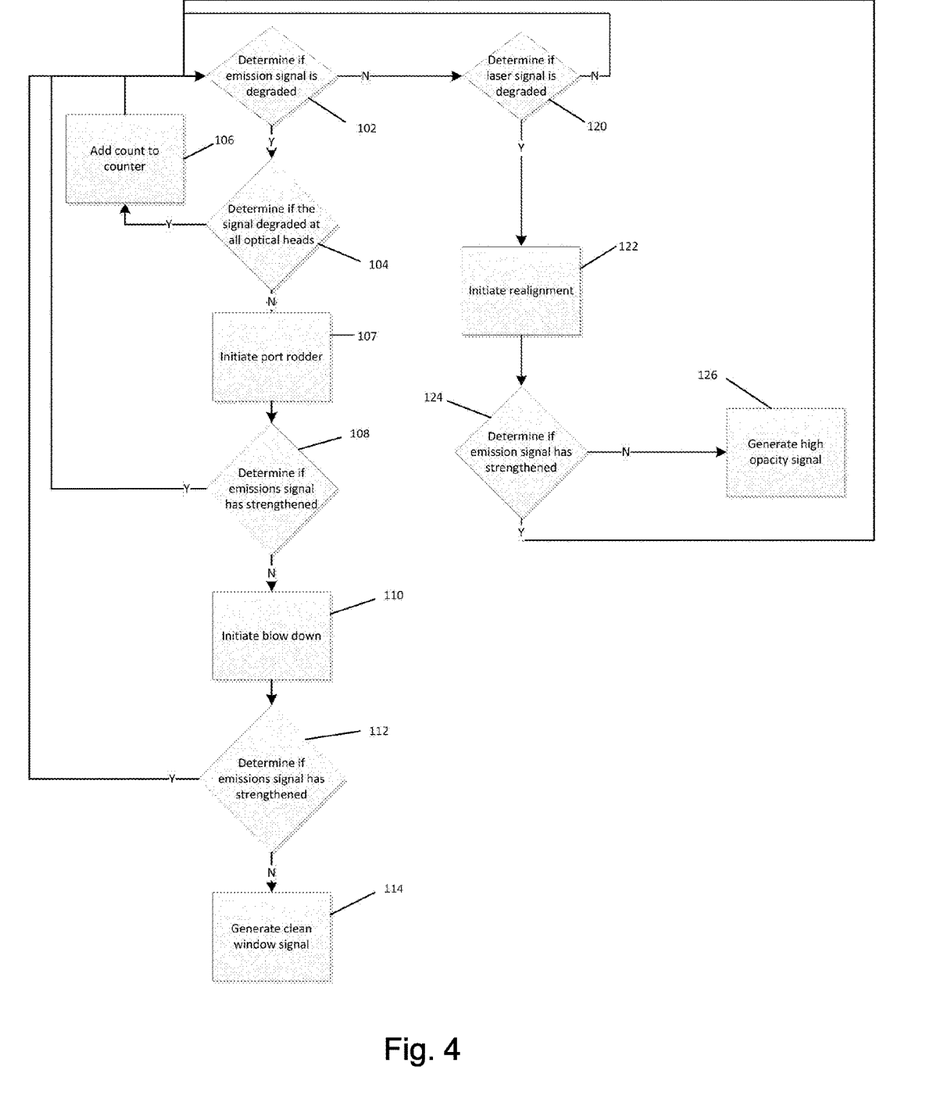
FIG. 4 is a flowchart illustrating a method for monitoring port blockage for TDLAS measurements in harsh environments.

A method for monitoring and clearing port blockage 100 is shown as a flow chart in FIG. 4. The method can be implemented on a general purpose or application specific computer such as the processor 46 in conjunction with the sensors as described below. In block 102, the processor 46 determines whether the emission signal for a photo sensor 80 has degraded with time. If it has, at block 104, the processor 46 determines whether emission signals from other TDLAS optical heads associated with the combustion chamber 68 have also degraded. If they have, at block 106, a count is added to a counter and the method continues at block 102. If the signal has not degraded at all the TDLAS optical heads, at block 107, the processor 46 initiates the port rodder 82 to clear debris from the sight tube. At block 108, the processor 46 determines whether emission signal has strengthened. If it has, some physical blockage has been removed and the process continues at block 102. If the signal has not strengthened, at block 110, the blow down apparatus 86 is initiated. At block 112, the processor 46 determines if the emission signal has strengthened. If it has, the blow down was successful and a physical blockage has been removed and the method continues at block 102. If the signal has not strengthened, at block 114, the processor 46 generates a clean window signal which may then initiate a process for cleaning the window.

If at block 102 the emission signal is not degraded, at block 120, the processor determines whether the laser signal is degraded. This may be accomplished, for example, by monitoring the strength of the signals from the optical detectors 42, 44 in the embodiment illustrated in FIG. 1. If the laser signal is not degraded, the method continues at block 102. If the laser signal is degraded the computer actuates the block per motors 72, 74 to realign the fiber collimator 71, at block 122. At block 124, a determination is made whether the realignment improves the laser signal. If it has, the laser path was misaligned and the process continues at block 102. If not, a high opacity signal is generated at block 126 and the method continues at block 102.

The method and apparatus for monitoring port blockage described herein allows remote and continuous monitoring of "continuity" of the light transmission path. The method and apparatus allow for a clear answer to the question of whether the ports in question are clear of debris or blocked. If the method and apparatus indicates a clear path and yet no signal is detected, there are a limited number of reasons remaining that could cause a loss of transmission such as particle loading leading to high opacity and optical misalignment. If the port indicates an obstructed path, steps can be taken to clear an obstruction and if clearing of the obstruction fails to solve the problem, a "clean window" signal could be generated to initiate cleaning of the window.

The description of the various embodiments has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiments described and shown in the figures were chosen and described in order to explain the principles of the invention, the practical application, and to enable others of ordinary skill in the art to understand the invention for various embodiments with various modifications as are suited to the particular use contemplated. All references cited herein are incorporated in their entirety by reference.

What is claimed is:

1. A method of monitoring blockage of a sight tube attached to a wall of a process chamber, the sight tube being operatively associated with a tunable diode laser absorption spectroscopy (TDLAS) optical head with a window between the sight tube and the TDLAS optical head, the method comprising:
monitoring, by a processor, an emission signal generated by a photo sensor and representative of light emitted by combustion within the process chamber, the photo sensor being located in the TDLAS optical head; and
determining, by the processor, that the emission signal is degrading as compared to a history of prior emission signals, wherein degrading of the emission signal indicates blockage of the site tube;
initiating, by the processor, clearing of the sight tube, when it is determined that the emission signal is degrading.

2. The method of claim 1, further comprising:
after clearing of the sight tube, determining, by the processor, if the emission signal has strengthened.

3. The method of claim 2 further comprising:
initiating, by the processor, window cleaning, when it is determined that the emission signal has not strengthened.

4. The method of claim 1 further comprising:
determining, by the processor, if the TDLAS laser signal emitted by the TDLAS optical head is degrading, when it is determined that the emission signal is not degrading.

5. The method of claim 4 further comprising:
initiating, by the processor, alignment of the optics of the TDLAS optical head, when it is determined that the TDLAS laser signal is degrading.

6. The method of claim 5 further comprising:
determining, by the processor, after aligning of the optics of the TDLAS optical head if the TDLAS laser signal is still degrading, and, when the TDLAS laser signal emitted by the TDLAS optical head is still degrading, producing a high opacity signal indicating presence of opacity within the process chamber.

7. The method of claim 1 wherein the step of initiating clearing comprises initiating a port rodder to clear physical blockage.

8. The method of claim 7 further comprising after initiating the port rodder, determining, by the processor, if the emission signal has strengthened.

9. The method of claim 8 further comprising initiating by the processor, blow down to clear physical blockage if the emission signal has not strengthened.

10. A method of monitoring blockage in a plurality of sight tubes attached to at least one wall of a process chamber, each sight tube being operatively associated with a tunable diode laser absorption spectroscopy (TDLAS) optical head with a window between the sight tube and the TDLAS optical head, the method comprising:
monitoring, by a processor, an emission signal generated by a photo sensor and representative of light emitted by combustion within the process chamber, the photo sensor being located in the TDLAS optical head; and
determining, by the processor, that an emission signal received by one of the photo sensors is degrading based on the emission signal as compared to a history of prior emission signals from the one of the photo sensors, wherein degrading of the emission signal indicates blockage of the site tube associated with the one of the photo sensors, and,
when it is determined that the emission signal received by the one photo sensor is degrading, determining, by the processor, if each emission signal received by the other photo sensors is degrading; and
initiating, by the processor, clearing of the sight tube associated with the one of the photo sensors, when it is determined that the emission signals generated by other of the photo sensors are not degrading.

11. The method of claim 10, further comprising:
when it is determined that the emission signals received by the other photo sensors are degrading, adding a count to a counter; and
repeating the steps of
determining, by the processor, if an emission signal received by one of the photo sensors is degrading based on the emission signal as compared to a history of prior emission signals from the one of the photo sensor, and,
when it is determined that the emission signal received by the one photo sensor is degrading, determining by the processor, if each emission signal received by the other photo sensors are degrading.

12. The method of claim 10, further comprising determining, by the processor, if a TDLAS laser signal emitted by the TDLAS optical head is degrading; and, initiating realignment of the TDLAS laser optical head when it is determined that the TDLAS laser signal emitted by the TDLAS optical head is degrading.

13. The method of claim 12, further comprising:
generating, by the processor, a high opacity signal indicating presence of opacity within the process chamber when it is determined that the emission signal from the one of the plurality of the photo sensors has not strengthened after initiating realignment.

14. The method of claim 10, further comprising determining if a TDLAS laser signal emitted by the TDLAS optical head is degrading; and,
when it is determined that the TDLAS laser signal emitted by the TDLAS optical head is not degrading, repeating the steps of:
determining, by the processor, if an emission signal received by one of the photo sensors is degrading based on the emission signal as compared to a history of prior emission signals from the one of the photo sensor, and,
when it is determined that the emission signal received by the one photo sensor is degrading, determining, by the processor, if each emission signal received by the other photo sensors is degrading.

* * * * *